United States Patent [19] [11] Patent Number: 6,030,981
Clement et al. [45] Date of Patent: Feb. 29, 2000

[54] PHENANTHRIDINE DERIVATIVES, METHODS OF PRODUCING THEM AND MEDICAMENTS CONTAINING PHENANTHRIDINE DERIVATIVES

[76] Inventors: Bernd Clement, Johann-Fleck-Str., Asse 27, D-24106, Kiel; Matthias Weide, Am Krähenholz 3, D-24220, Flintbek, both of Germany

[21] Appl. No.: 09/051,606

[22] PCT Filed: Oct. 11, 1996

[86] PCT No.: PCT/DE96/01958

§ 371 Date: Apr. 13, 1998

§ 102(e) Date: Apr. 13, 1998

[87] PCT Pub. No.: WO97/14683

PCT Pub. Date: Apr. 24, 1997

[30] Foreign Application Priority Data

Oct. 13, 1995 [DE] Germany ............................ 195 38 088

[51] Int. Cl.⁷ ........................ A61K 31/44; C07D 221/18
[52] U.S. Cl. ............................................. 514/284; 546/61
[58] Field of Search ................................ 514/284; 546/61

[56] References Cited

U.S. PATENT DOCUMENTS 5,747,502  5/1998  Hanaoka et al. ........................ 514/280

*Primary Examiner*—John Kight
*Assistant Examiner*—Charanjit S. Aulakh

*Attorney, Agent, or Firm*—Marshall & Melhorn

[57] ABSTRACT

The invention relates to phenanthridine derivatives of the general formula I and II

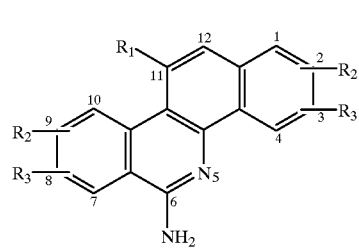

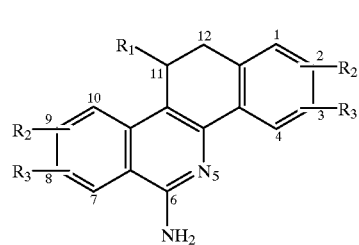

and also its salts, in which $R_1$ means a hydrogen atom, an aromatic, carbocyclic or hetercyclic or heterocyclic residue and in which $R_2$ and $R_3$, which can be the same or different, mean a hydrogen atom, an alkyloxy residue, an alkylenoxy residue, a halogen atom or a nitro group.

14 Claims, 5 Drawing Sheets

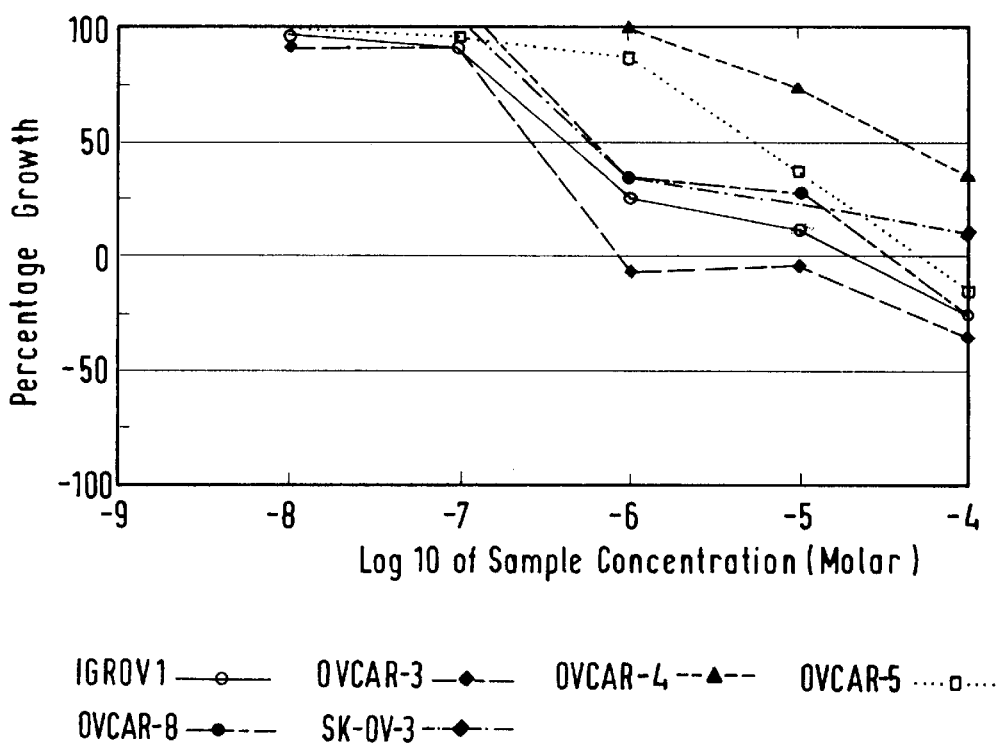
FIG. 5 Ovarian Cancer
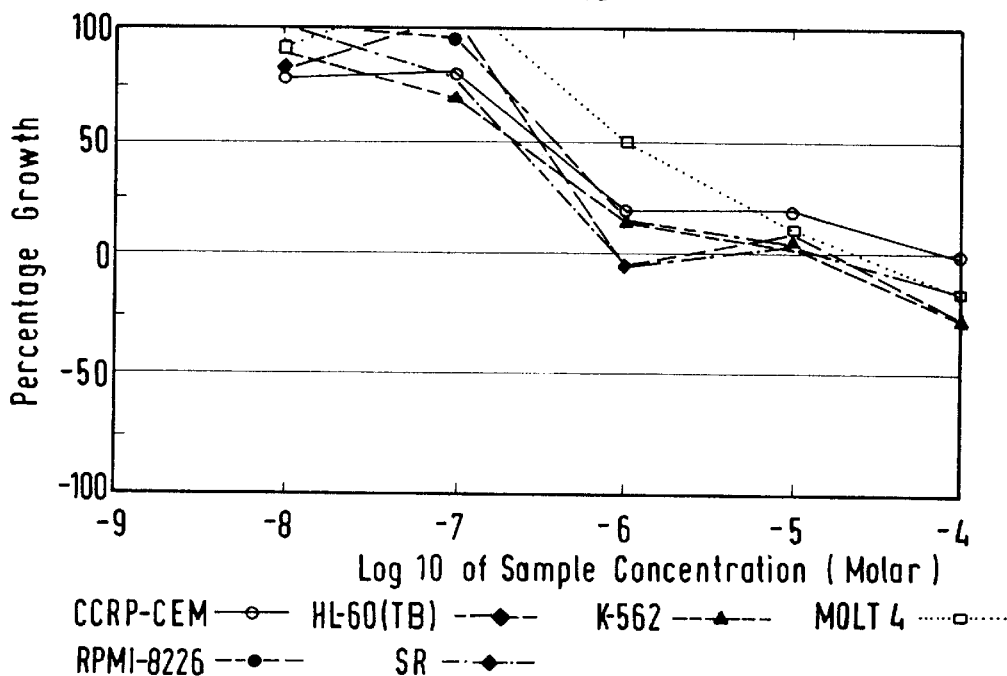
FIG. 6 Leukemia

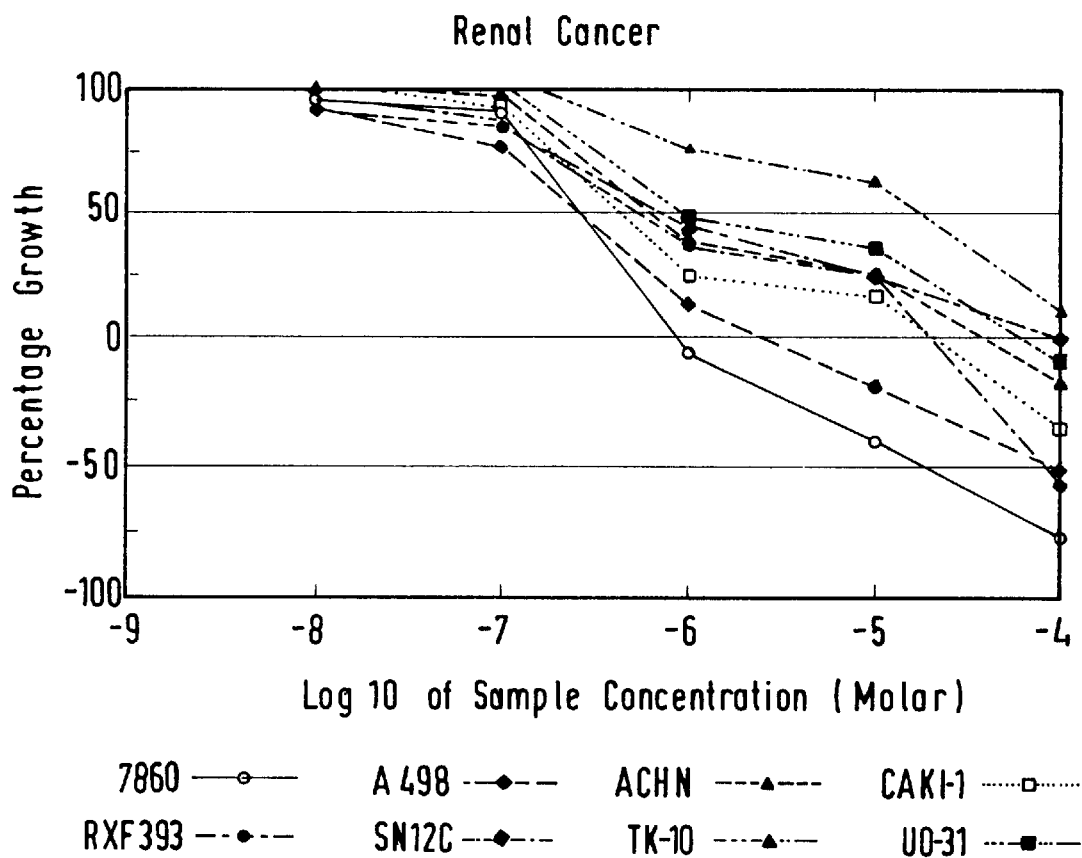

PHENANTHRIDINE DERIVATIVES, METHODS OF PRODUCING THEM AND MEDICAMENTS CONTAINING PHENANTHRIDINE DERIVATIVES

This application is a 371 of PCT/DE 96/01958, now WO 97/14683 published Apr. 24, 1997.

BACKGROUND OF THE INVENTION

The invention relates to new phenanthridine derivatives, which have an amino-group in position 6, a method for their production and for producing medicines containing phenanthridine derivatives.

Presently known syntheses of benzo(c)phenanthridine, its 11,12 dihydro-derivatives and similar compounds are very complex. The methods of Robinson et al. concerning the Bischler-Napieralski cyclisation and also of Ninomiya et al. using photocyclisation by Enamiden or by Shamma et al. and Cushman et al. concerning the Dickman-Thorpe-cyclisation should be mentioned here, said methods all extending over a great number of reaction steps (see I. Ninomya and T. Naito: Synthesis of the benzo(c)phenanthridine alkaloids. Recent. Dev. Nat. Carbon compd. 10, 11-90 (1984) and the literature mentioned there). p Furthermore, benzo(c)phenanthridine derivatives and their anti-tumour effect are known from Pharmacy 44 pp. 593–597 (1989). Further phenanthridine derivatives are described in Tetrahedron 49 pp. 10305–10316 (1993) and in J. Chem. Soc. Perkin Trans. I, pp. 1137–1140 (1983) and in J. Me. Chem. 36, pp. 3686–3692 (1993). In the publications in J. Med. Chem. and Tetrahedron, derivatives with an amino-group in position 6 were also indeed described, said amino-group being substituted however in every case. Other derivatives have up till now not become known. This can be attributed mainly to the fact that the presently known derivatives are based on synthesis methods which are costly and complex. Therefore production of other phenanthridine derivatives was up till now not possible.

OBJECT OF THE INVENTION

This assumed, it is the object of the present invention to make known new phenanthridine derivatives, a method for their production and their application.

The object is achieved, with respect to the phenanthridine derivatives, by the characterising features of claim 1 and, with respect to the production method, by the features of claim 5. The application according to the invention of these phenanthridine derivatives is mentioned in claim 10. The subclaims demonstrate advantageous further developments.

According to claim 1, the new phenanthridine derivatives are defined by the general formulae I and II,

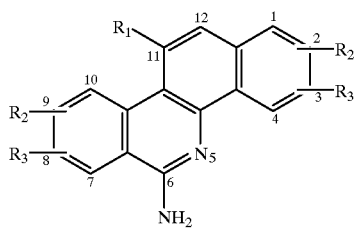

I

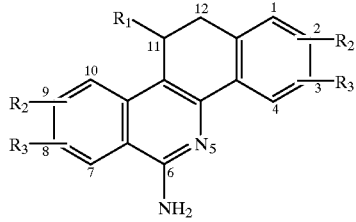

II in which $R_1$ means a hydrogen atom, an aromatic or heterocyclic residue, and $R_2$ and $R_3$, which can be the same or different, mean hydrogen atoms an alkyl-oxy residue, an alkylene-oxy residue, a halogen atom or a nitro group.

By an aromatic carbocyclic residue $R_1$ can be understood particularly such residues as are derived from benzene, naphthalene, anthracine, phenanthrene and pyrene. By an aromatic heterocyclic residue $R_1$ can be understood particularly residues, which are derived from furane, thiophene, pyridine, 1,2,4-oxdiazole, 1,2,3-triazole, benzofurane, benzoxazole, benzimidazole, benzthiazole, also the corresponding naphtho-analogues of the type named benzo-five ring heterocyclenes and from indole, quinolene and isoquinolene. The aromatic carbocyclic or heterocyclic residues can be substituted once or several times.

For this purpose, as substitutes under the reaction conditions, inert groups and/or atoms may be considered such as mono-amino groups, alkyl amino groups, dialkyl amino groups, alkyl groups, alkoxyl groups, alkylene oxy groups and halogens.

On the basis of the found pharmacological characteristics, the derivatives which are of particular importance are those in which $R_2$ and $R_3$ hydrogen, and $R_1$ hydrogen are an unsubstituted phenyl residue, a phenyl residue with one or several methoxyl groups or a N,N-dimethyl amino function. For this purpose, those derivatives in which $R_1$ is a substituted or unsubstituted phenyl residue, in particular 2,4-dimethoxyphenyl or 3,4-dimethoxyphenyl, may be emphasized. The 2,4-dimethoxyphenyl derivative is particularly preferred here. The phenanthridine derivatives according to the invention readily form physiologically acceptable salts. Such salts are e.g. salts with inorganic and organic acids, e.g. dihydrochloride, hydrobromide and sulphates. Particularly well suited salts of organic acids are formed with aliphatic mono- and di-carbon acids. Examples of such salts are acetates, maleates and fumarates.

The compounds were able to be confirmed by IR- and HNMR-analysis.

The invention relates furthermore to a method for producing phenanthridine derivatives. The applicant was able to show surprisingly that it is possible to obtain the phenanthridine derivatives according to the invention by smean replacing appropriately substituted aldehydes with appropriately substituted methobenzonitrile. Carrying on in detail at this stage with transformation of an aldehyde of Formula III $R_1$—CHO   III $R_1$ having the previously mentioned meaning and with 2 mol of a 2-methylbenzonitrile of Formula IV

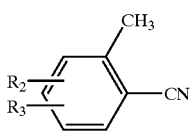

and $R_2$ and $R_3$ having the previously mentioned meaning, are introduced in the presence of a base and an aprotic dipolar solvent and after isolation in a further step according to generally valid methods, dehydration results with an appropriate dehydration medium in the presence or absence of solvent. The reaction process can be represented as follows:

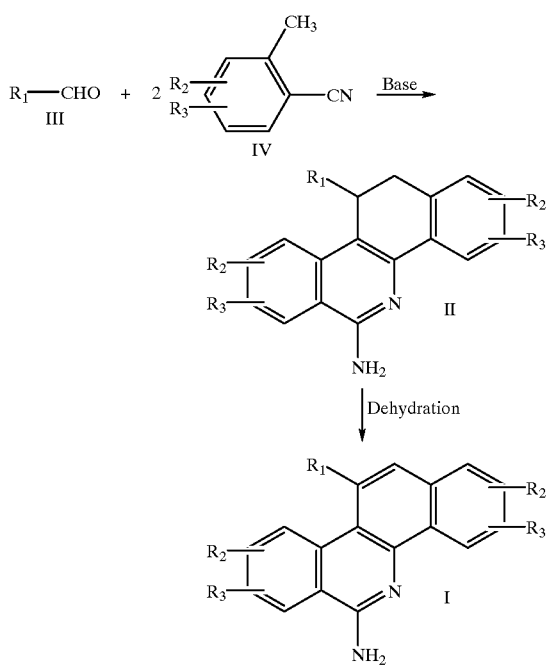

Preferably, amides such as dimethylformamide, dimethylacetamide, diethylacetamide, hexamethylphosphoric acidtrisamide and carbamides such as tetramethyl carbamide, 1,3-dimethyltetrahydro-2-pyrimidinon and 1,3-dimethylimidazolidinon or dimethylsulphoxide may be used as aprotic dipolar solvent for the reaction according to the invention.

Alkali hydrides or alkaline earth hydrides such as sodium hydride, alkali amides such as sodium amide, sodium methyl acetamide, alkali alcoholate, alkaline earth alcoholates or aluminum alcoholates such as potassium-tert-butylate, sodium methylate, sodium ethylate or aluminium ethylate can for example be used as a base.

The reaction can be conducted as follows: on to a solution of a base in an appropriate dipolar aprotic solvent, a solution of the compounds III and IV in the same solvent is dropped slowly in an inert gas atmosphere. After agitating for several hours at 35° C. to 50° C. in an inert gas atmosphere the product is poured on to ice-cold water and shaken out with an appropriate organic solvent. The organic phase is reduced and, separated from the residue by introducing a halogen hydrogen acid or by shaking with an appropriate inorganic or organic acid, the 6-amino-11,12-dihydrobenzo(c)phenanthridine II is precipitated or is isolated, by using an aqueous acid solution, from the aqueous phase after neutralisation and removal of the base. The 6-amino-11,12-dihydrobenzo(c)phenanthridine II can then be dehydrated to the 6-aminobenzo(c)phenanthridine I, according to generally accepted methods, with an appropriate dehydration medium in the presence or absence of an inert solvent.

It should be emphasized especially, in the method according to the invention, that phenanthridine derivatives, which have a substituted or an unsubstituted phenyl residue in position-11, are hereby synthesized. It is surprising that the synthesis is possible by means of the simple reaction which is described here, in which a great variation in range exists on the basis of the original substances which are put in with respect to the educts which can be obtained.

It was then found that the previously described phenanthridine derivatives possessed excellent anti-tumour, anti-microbial, anti-fungicidal, anti-viral and anti-inflammatory properties. In order to examine the pharmacological properties, the compounds of the general Formula I and II were examined in an "in-vitro-Antitumor-Screening" of the National Cancer Institute (NCI), Bethesdal, Md., USA. About 58 different human pathogenic tumour cell series, which stemmed from nine types of cancer (leukaemia, non-small cell lung carcinoma, large intestine cancer, central nervous system cancer, melanoma, ovarian cancer, renal cancer, prostate cancer and breast cancer). In order to determine the level of efficacity, tumour cells were subjected to the compounds over two days and subsequently the inhibition of growth was determined indirectly via the calculation of the protein biomass with sulphorhodomine B. Untreated cultures served as a reference.

In these experiments, 6-amino-11-(2,4-dimethoxyphenyl)benzo(c)phenanthridiniumperchlorate for example showed inhibitions of growth. Surprisingly, the compound indicates activities which lie outwith the category of anti-tumour compounds studied in a similar manner, with the result that a completely new spectrum of effect is achieved.

BRIEF DESCRIPTION OF THE DRAWINGS

From the present data, dosage-effect curves are depicted in FIGS. 1 to 9 for this compound for example. The nine different figures contain the various forms of cancer. The percentage growth respectively is plotted with respect to the concentration of compound (as $\log_{10}$ of the molar concentrations). The individual curves of each type of cancer are different cell strains of this form of cancer, which appear as keys in their normal abbreviations. Horizontal lines in the Figures indicate percentage growth of +100, +50, 0, -50 and -100. 100% growth indicates for example no change in growth after two days without supplement of substance. It can be seen in the individual curves that with increasing concentrations of the substance the percentage growth declines.

DETAILED DESCRIPTION OF THE PREFERRED EMBODIMENT

Figure 1:
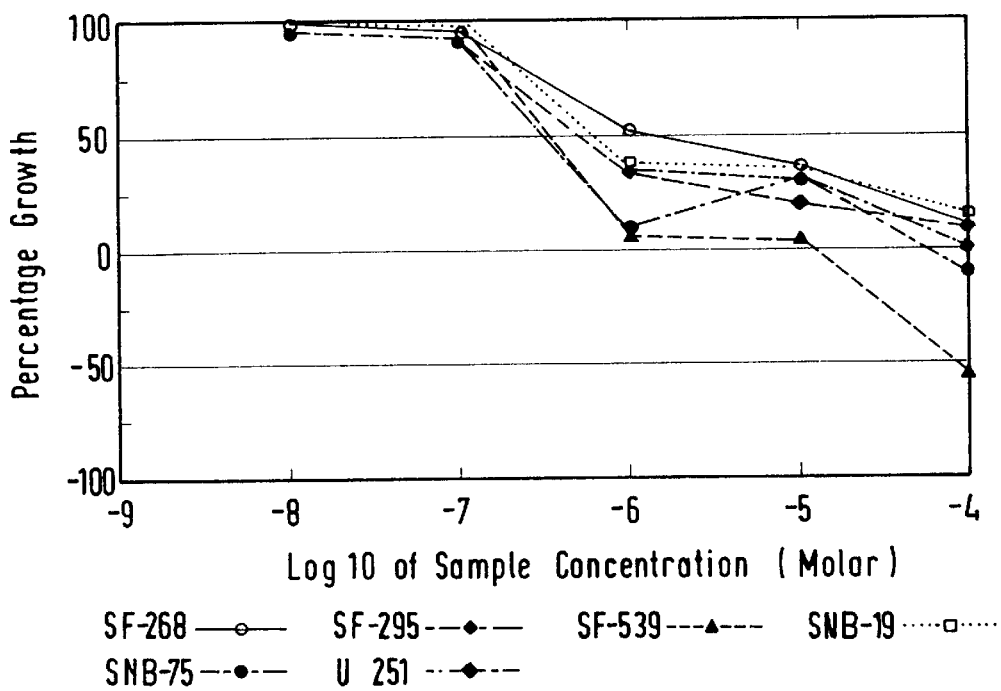
Figure 2:
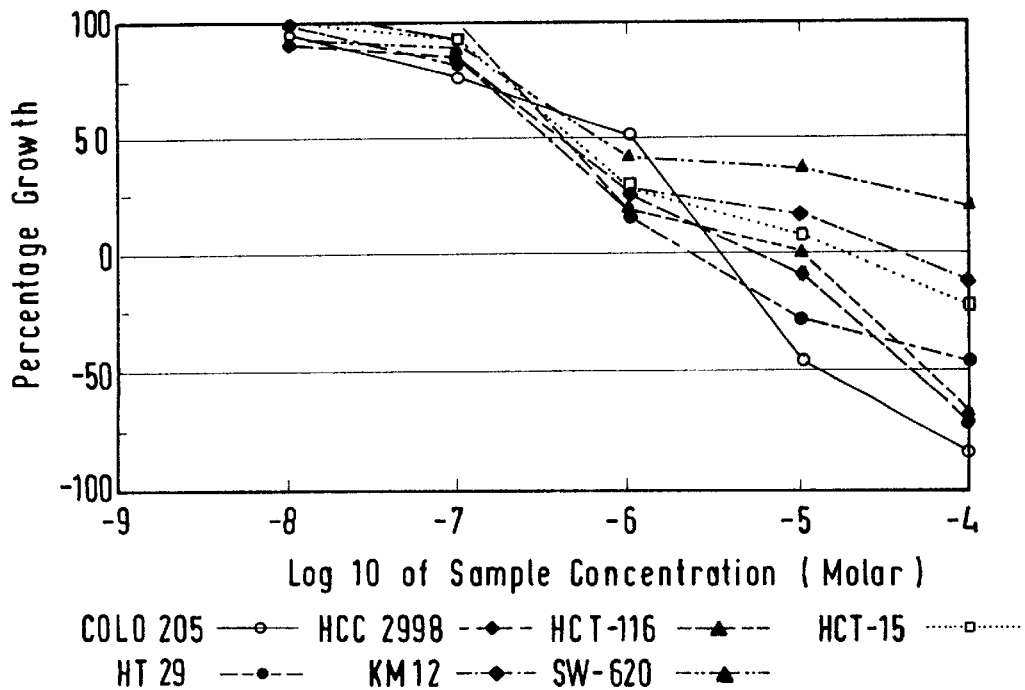
Figure 3:
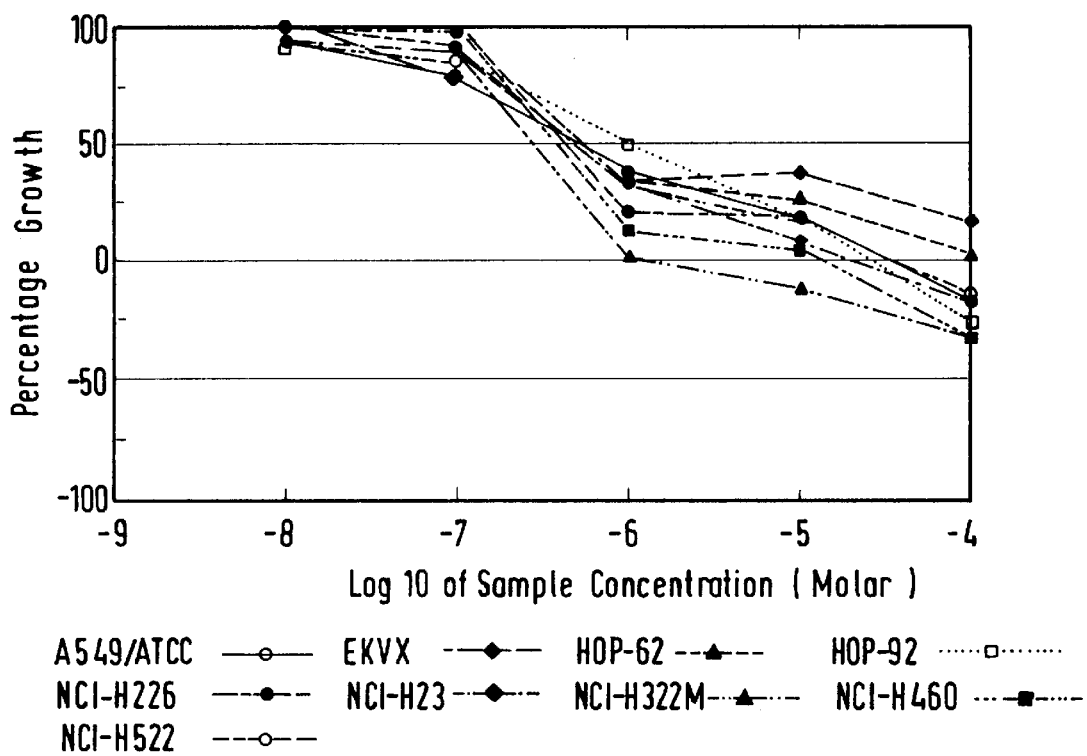
Figure 4:
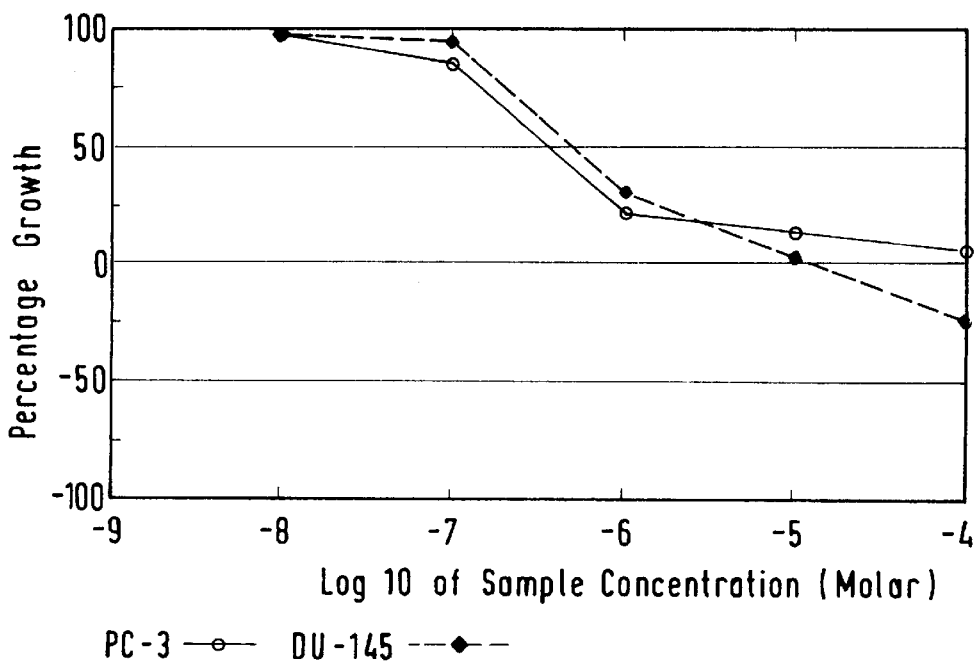
Figure 7:
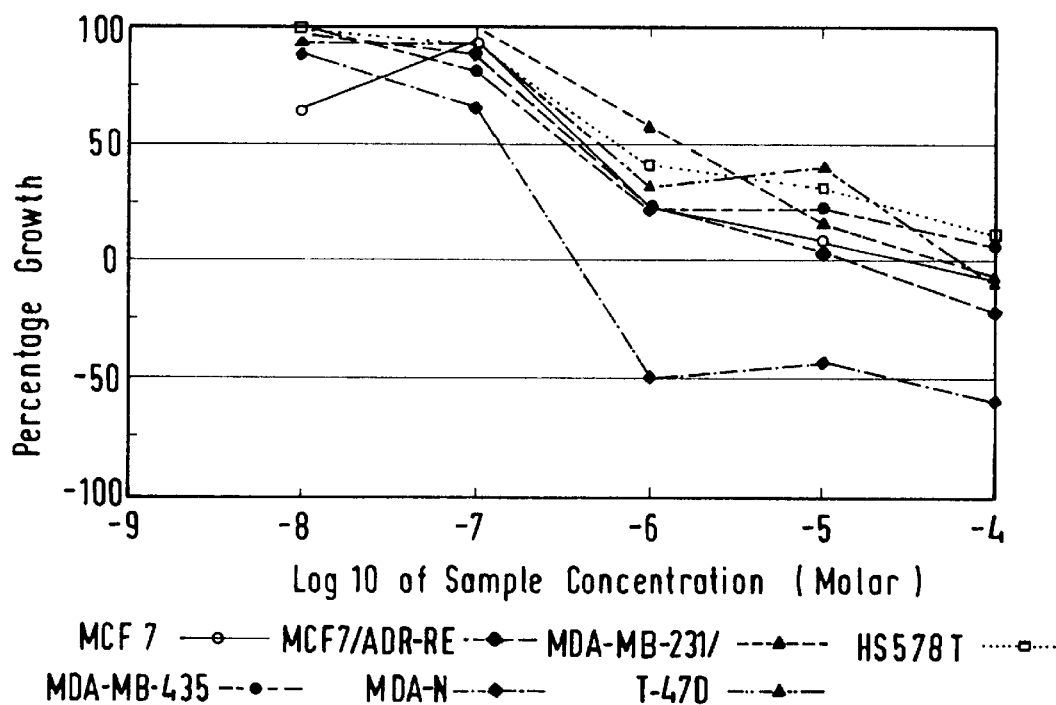
Figure 8:
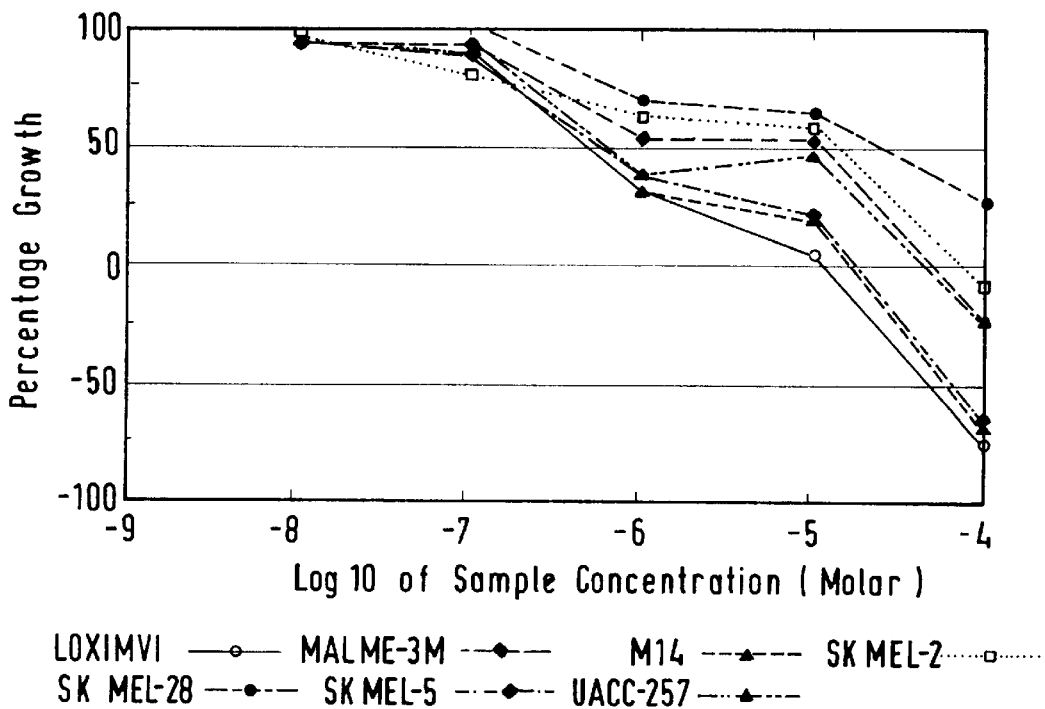

The invention also relates therefore to medicines containing phenanthridine derivatives which are described here. The medicine contains, for this purpose, at least one phenanthridine derative, in the manner described here, together with at least one inert pharmaceutically acceptable carrier or dilution medium. A derivative of the general Formula 1 is preferred as a phenanthridine derivative in which $R_1$ is a 2,4-methoxyphenyl residue and $R_2$ and $R_3$ are hydrogen. The compound, according to the invention, can be administered orally, topically or parenterally, or in the form of suppositories. The preferred mode of administration is oral administration. This can be administered in the form of the base or as a physiologically acceptable salt. It is generally mixed with a pharmaceutically acceptable carrier or dilution medium, in order to create a medicine. For oral administration the medicine can be made available most usefully in the form of capsules or tablets or possibly even slow-release tablets. They can also be available in the form of dragees or in syrup form. Suitable topic preparations are e.g. salts, lotions, creams, powders and sprays.

In the following, the invention is described in greater detail with the help of several embodiment examples.

EMBODIMENTS

Production of the 6-amino-11,12-dihydrobenzo(c) phenanthridine II:

EXAMPLE 1

6-amino-11,12-dihydrobenzo(c)phenanthridiniumchloride

A solution of 2.47 g (22 mmol) KOBu$^r$ in 20 ml DMPU in a nitrogen atmosphere is prepared and a solution of 300 mg (10 mmol) paraformaldehyde and 2.34 g (20 mmol) 2-methylbenzonitrile in 12 ml DMPU is dropped slowly into the preparation in portions of 2 ml at a spacing of 15 minutes in a contra-flow of nitrogen. After six hours' agitation at 35° C. in a nitrogen atmosphere the product is poured on to a solution of 2.2 g (40 mmol) ammonium chloride in 100 ml ice water and shaken out three times with 100 ml dichloromethane. The combined organic phases are filtered through wadding, rotated to approx. 100 ml and shaken vigorously with 3 N hydrochloric acid. The detached organic phase is further rotated until there is heavy precipitation, then being placed in the fridge overnight. The precipitation is stopped, washed with a little dichloromethane, dried and recrystallised out of methanol/dichloromethane. 6-amino-11,12-dihydroben-zo(c)phenanthridiniumchloride is obtained. Pale yellow platelets, yield: 16% of theoretical yield, melting point 350° C.—IR (KBr): ν=3244 cm$^{-1}$, 3102, 2946, 1654, 1630, 1616.—$^1$H NMR (360 MHz, [D$_6$] DMSO): δ=3.0 (mc, 2H, —CH$_2$—), 3.08 (mc, 2 H, —CH$_2$—), 7.43 (mc, 3H, Ar—H), 7.77 (t, 1H, Ar—H), 8.02 (t, 1H, Ar—H), 8.16 (d, 1H, Ar—H), 8.27 (mc, 1H, Ar—H), 8.60 (d, 1H, Ar—H), 9.49 (br, 2H, —NH$_2$), 13.78 (br, 1H, ≡N$^+$—H). C$_{17}$H$_{15}$N$_2$Cl(292.77) Ber. C, 72.21; H, 5.35; N, 9.91; Gef. C, 72.13; H, 5.35; N, 9.99.

EXAMPLE 2

6-amino-11,12-dihydro-11-phenylbenzo(c) iphenanthridiniumchloride

A solution of 1.06 g (10 mmol) benzaldehyde and 2.34 g (20 mmol) 2-methylbenzonitrile in 5 ml DMPU is dropped slowly into a solution of 2.47 mg (22 mmol) KOBu$^r$ in 20 ml DMPU in a nitrogen gas atmosphere. After five hours' agitation at 35° C. in a nitrogen gas atmosphere the product is poured on to a solution of 2.2 g (40 mmol) ammonium chloride in 100 ml ice water, and shaken out three times with 100 ml dichloromethane. The organic phase is filtered through wadding and rotated roughly to 100 ml and shaken vigorously with 3 N hydrochloric acid. The resulting precipitation is suctioned off, washed with dichloromethane and dried. After recrystallisation from methanol/dichloromethane 6-amino-11,12-dihydro-11-phenylbenzo (c)-phenanthridiniumchloride is obtained. Bright yellow platelets, yield: 52% of theoretical yield, melting point 355° C.—IR (KBr): ν=3446 cm$^{-1}$, 3076, 1662, 1620, 1570.—$^1$H NMR (400 MHz, [D$_6$] DMSO): δ=3.18 (mc, 1H, 12-H), 3.56 (mc, 1H, 12-H), 4.95 (mc, 1H, 11-H), 7.09 (mc, 5H, C6H5-), 7.24 (d, 1H, Ar—H), 7.35 (t, 1H, Ar—H), 7.44 (t, 1H, Ar—H), 7.74 (mc, 1H, Ar—H), 7.91 (mc, 2H, Ar—H), 8.3 (d, 1H, Ar—H), 8.61 (d, 1H, Ar—H), 9.3 (br, 2H, —NH$_2$,), 13.7 (br, 1H, ≡N$^+$—H).

C$_{23}$H$_{19}$N$_2$Cl(358.87) Ber. C, 76.98; H 5.34; N, 7.81; Gef. C, 76.52; H, 5.37N, 7.75.

EXAMPLE 3

6-amino-11,12-dihydro-11-(3,4-dimethoxyphenyl)benzo[c] phenanthridiniumchloride

Similar to Example 1. Light-yellow needles. Yield: 53% of theoretical yield, melting point 205° C. (methanol/water). -IR (KBr): ν=3438 cm-, 3268, 3106, 2938, 1648, 1616, 1584.—$^1$H NMR (400 MHz, [D6] DMSO): δ=3.08 (mc, 1H, 12-H), 3.42 (mc, 1H, 12-H), 3.61 (s, 3H, —OCH$_3$), 3.99 (s, 3H, —OCH$_3$), 5.02 (mc, 1H, 11-H), 6.04 (mc, 1H, Ar—H), 6.21 (mc, 1H, Ar—H), 6.61 (mc, 1H, Ar—H), 7.20 (d, 1H, Ar—H), 7.34 (t, 1H, Ar—H), 7.43 (t, 1H, Ar—H), 7.63 (d, 1H, Ar—H), 7.73 (t, 1H, Ar—H), 7.91 (t, 1H, Ar—H), 8.36 (d, 1H, Ar—H), 8.61 (d, 1H, Ar—H), 9.56 (br, 2H, —NH$_2$), 13.85 (br, 1H, ≡N$^+$—H).

C$_{25}$H$_{23}$N$_2$O$_2$Cl (418. 92) Ber. C, 71.68; H, 5.53; N, 6.69; Gef. C, 70.95; H, 5.37; N, 6.80.

Production of 6-aminobenzo(c)phenanthridine I:

EXAMPLE 1

6-aminobenzo(c)phenanthridiniumperchlorate

A solution of 404 mg (1.7 mmol) DDQ in 35 ml dioxan is added to a solution of 250 mg (1.02 mmol) 6-amino-11, 12-dihydrobenzo(c)phenanthridine in 15 ml dioxan and heated for four hours in a contra-flow situation. The cooled solution is subsequently poured on to a sodium hydrogen carbonate solution and shaken out with diethyl ether. The diethyl ether phase is washed once with diluted sodium hydrogen carbonate solution and three times with water. After addition of 70% perchloric acid, precipitation is obtained. After drying out and recrystallising from methanol, brown needles, yield: 44% of theoretical yield, melting point 325° C. -IR (Kbr):ν=3404 cm$^{-1}$, 3348, 3298, 3276, 3234, 1666, 1616.—$^1$H NMR (300 MHz, [D$_6$] DMSO): δ=7.82 (mc,3H, Ar—H), 8.0 (d, 1H, Ar—H), 8.13 (mc, 2H, Ar—H), 8.56 (mc, 2H, Ar—H), 8.69 (d, 1H, Ar—H), 8.83 (d, 1H, Ar—H), 9.73 (br, 2H, —NH$_2$), 12.84 (br, 1H, ≡N$^+$—H).

C$_{17}$H$_{13}$N$_2$O$_4$Cl (344.06) Ber. C, 59.29; H, 3.81; N, 8.14; Gef. C, 59.23; H, 3.83; N, 8.24.

EXAMPLE 2

6-amino-11-phenylbenzo[c]phenanthridiniumperchlorate

Similar to Example 1. Grey-brown needles, yield: 50% of theoretical yield, melting point 345° C. -IR (KBr) ν=3412 cm$^{-1}$, 3358, 3310, 3226, 1668, 1642, 1612.—$^1$H NMR (300 MHz, [D6]DMSO): δ=7.51 (mc, 7H, Ar—H), 7.80 (mc, 4H, Ar—H), 8.15 (d, 1H, Ar—H), 8.66 (mc, 2H, Ar—H), 9.88 (br, 2H, —NH$_2$), 12.8 (br, 1H, ≡N$^+$—H).

C$_{23}$H$_{17}$N$_2$O$_4$Cl (420.09) Ber. C, 65.70; H, 4.08; N, 6.67; Gef. C, 65.67; H, 4.03; N, 6.67.

EXAMPLE 3

6-amino-11-(2,4dimethoxyphenyl)benzo[c] phenanthridiniumperchlorate

Similar to Example 1. Dark brown needles, yield: 45% of theoretically yield, melting point 336° C. -IR (KBr): ν=3418 cm$^{-1}$, 3352, 3302, 3270, 1660, 1608.—$^1$H NMR (300 MHz, [D6] DMSO): δ=3.38 (s, 3H, —OCH$_3$), 3.87 (s, 3H, —OCH$_3$), 6.69 (mc, 1H, Ar—H), 6.77 (mc, 1H, Ar—H), 7.34 (mc, 1H, Ar—H), 7.77 (mc, 6H, Ar—H), 8.11 (mc, 1H, Ar—H), 8.77 (mc, 2H, Ar—H), 9.72 (br, 2H, —NH$_2$); 12.58 (br, 1H, ≡N$^+$—H).

C$_{25}$H$_{21}$N$_2$O$_6$Cl (480.19) Ber. C, 62.49; H, 4.41; N, 5.83; Gef. C, 62.56; H, 4.30; N, 5.87.

We claim:
1. A phenanthridine derivative of the Formula I and II

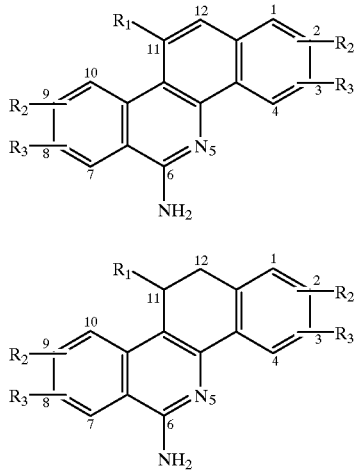

or their salts, wherein $R_1$ is selected from the group consisting of aromatic carbocyclic and heterocyclic residues, the heterocyclic residues are residues derived from the group consisting of furane, thiophene, pyridine, 1,2,4-oxdiazole, 1,2,3-triazole, benzofurane, benzoxazole, benzimidazole, benzthiazole, corresponding naptho-analogues of the type named benzo-five ring heterocyclenes, indole, quinolene, and isoquinolene and $R_2$ and $R_3$ are the same or different and are selected from the group consisting of hydrogen, alkyoxy residues, alkylene oxy residues, halogen atoms and nitro groups.

2. The phenainthridine derivative according to claim 1, wherein $R_2$ and $R_3$ are hydrogen and $R_1$ is selected from the group consisting of unsubstituted phenyl residues, phenyl residues with at least one methoxy group, and phenyl residue with a N,N-dimethylamine.

3. The phenanthridine derivative according to claim 2, wherein $R_1$ is selected from the group consisting of phenyl residues, 2,4-methoxyphenyl residues and 3,4-methoxyphenyl residues.

4. The phenanthridine derivative according to claim 3, wherein $R_1$ is a 2,4-methoxyphenyl residue.

5. A method for producing the phenanthridine derivative of the Formula II according to claim 1, comprising: causing an aldehyde of the Formula III

$R_1$—CHO to react with a 2-methylbenzonitrile of the Formula IV

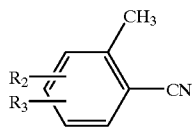

in the presence of bases in an aprotic, dipolar solvent, the residues $R_1$, $R_2$ and $R_3$ possessing the meanings mentioned in claim 1 and with the proviso that $R_1$ can also be hydrogen.

6. A method for producing the phenanthridine derivative of the general Formula I according to claim 1, comprising: causing an aldehyde of the Formula III

$R_1$—CHO to react with a 2-methylbenzonitrile of the Formula IV

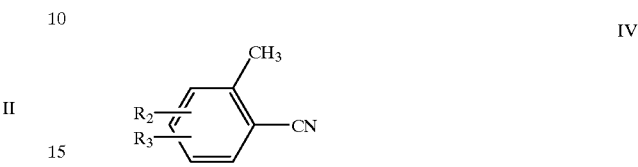

in the presence of a base in an aprotic, dipolar solvent, the residues $R_1$, $R_2$ and $R_3$ possessing the meanings mentioned in claim 1 and with the provisio that $R_1$ can also be hydrogen and dehydrating a product of the reaction with a dehydration medium in the absence or presence of solvents.

7. The method for producing phenanthridine derivatives according to claim 5, wherein an aldehyde of the Formula III is caused to react, $R_1$ being selected from the group consisting of phenyl residues, 2,4-methoxyphenyl residues, 3,4-methoxyphenyl residues and hydrogen.

8. The method according to claim 6, wherein an aldehyde of the Formula III is caused to react, $R_1$ being selected from the group, consisting of phenyl residues, 2,4-methoxyphenyl residues, 3,4-methoxyphenyl residues and hydrogen.

9. The method according to claim 7, wherein $R_1$ is selected from the group consisting of 2,4-methoxyphenyl residues and 3,4-methoxyphenyl residues.

10. The method according to claim 8, wherein $R_1$ is selected from the group consisting of 2,4-methoxyphenyl residues and 3,4-methoxyphenyl residues.

11. The method according to claim 5, wherein a 2-methylbenzonitrile of the Formula IV is caused to react, $R_2$ and $R_3$ being hydrogen.

12. The method according to claim 6, wherein a 2-methylbenzonitrile of the general Formula IV is caused to react, $R_2$ and $R_3$ being hydrogen.

13. A pharmaceutical composition comprising therapeutically effective amount of at least one of the phenanthridine derivatives of claim 1 together with at least one inert, pharmaceutically acceptable carrier or dilution medium.

14. The pharmaceutical composition according to claim 13, comprising therapeutically effective amount of a phenanthridine derivative of the Formula I, $R_1$ being a 2,4-methoxyphenyl residue and $R_2$ and $R_3$ being hydrogen.

* * * * *